United States Patent [19]

Kuhla et al.

[11] Patent Number: 4,721,721

[45] Date of Patent: Jan. 26, 1988

[54] 6-(4-THIAZOLE) COMPOUNDS, CARDIOTONIC COMPOSITIONS INCLUDING THE SAME, AND THEIR USES

[75] Inventors: Donald E. Kuhla, Doylestown; Henry F. Campbell, Lansdale; William L. Studt, Harleysville, all of Pa.

[73] Assignee: Rorer Pharmaceutical Corporation, Fort Washington, Pa.

[21] Appl. No.: 683,204

[22] Filed: Dec. 18, 1984

[51] Int. Cl.$^4$ .................... A61K 31/47; C07D 215/22
[52] U.S. Cl. .................... 514/312; 546/157; 546/158; 548/154
[58] Field of Search ............... 514/312, 314, 227, 222, 514/253; 546/157, 158; 548/154; 544/58.6, 128, 363

[56] References Cited

U.S. PATENT DOCUMENTS 2,969,369  1/1961  Krimmel .................... 548/154
4,418,070  11/1983  Okonogi .................... 548/182

FOREIGN PATENT DOCUMENTS 0009780  1/1982  Japan .................... 546/157
82/01706  5/1982  PCT Int'l Appl. ............ 546/157

Primary Examiner—Sidney Marantz
Assistant Examiner—Robert Benson
Attorney, Agent, or Firm—James A. Nicholson; Alexis Barron; Martin F. Savitzky

[57] ABSTRACT

Cardiotonic fused aromatic bicyclic ring substituted thiazole compounds and their salts, methods for increasing cardiac contractility in humans and other mammals by the use of said compounds, pharmaceutical compositions including said compounds and methods for compound preparation.

22 Claims, No Drawings

6-(4-THIAZOLE) COMPOUNDS, CARDIOTONIC COMPOSITIONS INCLUDING THE SAME, AND THEIR USES

FIELD OF THE INVENTION

This invention relates to novel bicyclic heteroaryl substituted thiazoles useful as cardiotonic agents for the treatment of congestive heart failure. This invention also relates to methods for increasing cardiac contractility using said compounds, pharmaceutical compositions and methods for the preparation of said compounds.

Congestive heart failure is a life-threatening condition in which myocardial contractility is depressed so that the heart is unable to adequately pump the blood returning to it. Normal pathologic sequelac include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Inotropic drugs include the 5-pyridyl substituted pyridones disclosed in U.S. Pat. Nos. 4,004,012; 4,072,746; 4,107,315; 4,137,233; 4,199,586; 4,271,168; and 4,107,315; in GB No. 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572 and the 5-phenyl-thiazole compounds disclosed in U.S. Pat. No. 4,418,070.

Cardiotonic bicyclic heteroaryl-5-substituted pyridyl compounds are disclosed in U.S. Ser. No. 410,646, and cardiotonic diazaheterocyclic-5-substituted pyridyl compounds are disclosed in U.S. Pat. No. 4,432,979 and U.S. Ser. Nos. 314,692 and 493,336, all of which are assigned to the same assignee as the present application.

SUMMARY OF THE INVENTION

The present invention relates to a class of bicyclic N-heteroaryl ring substituted thiazoles which exhibit cardiotonic activity in humans and mammals.

The more preferred compounds of the present invention include thiazoles substituted by a bicyclic N-heteroaryl ring and where the total number of carbon atoms in the bicyclic ring is no greater than about ten.

This invention relates particularly to the bicyclic lactam compounds within the scope by Formula I:

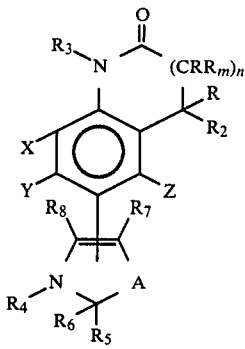

wherein:
m is 1 or 2;
n is 0, 1, or 2;
$R_m$ is $R_1$ or $R_2$, when m is 1 or 2, respectively;
A is N or S, provided that A is N only when A and $R_6$ together form a double bond in an imidazo[2.1-b]thiazole ring system;
X, Y and Z are each independently hydrogen, alkyl, alkoxy, hydroxy, alkylmercapto, alkylsulfinyl or alkylsulfonyl;
R and $R_3$ are each independently hydrogen or lower alkyl;
$R_1$ and $R_2$ are each independently hydrogen, lower alkyl or both $R_1$ and $R_2$ form a carbon-carbon double bond;
$R_4$ and $R_5$ together form a carbon-nitrogen double bond or together with the atoms to which they are attached form an imidazo[2.1-b]thiazole ring system including two additional carbon atoms and either one sulfur atom or one additional nitrogen atom;
$R_6$ is hydrogen, alkyl, aryl, amino, arylamino, mono- or di-alkylamino, aralkylamino, guanidino, amidino, hydroxyl, hydroxyalkyl, hydroxyalkylamino, aminoalkylamino, di-alkylaminoalkylamino, aminoalkyl, mono- or di-alkylaminoalkyl,

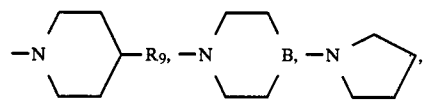

or together with either $R_5$ or A form a carbon-heteroatom double bond in said imidazo[2.1-b]thiazole ring system;
$R_7$ and $R_8$ are hydrogen, lower alkyl or one of $R_7$ or $R_8$ represents the carbon-carbon single bond to the position on the fused bicyclic ring ortho to the Y and Z groups, provided that one of $R_7$ or $R_8$ is other than hydrogen or lower alkyl;
$R_9$ is H, alkyl or aryl;
B is $NR_{10}$, oxygen or sulfur; and
$R_{10}$ is H, alkyl, aryl, or

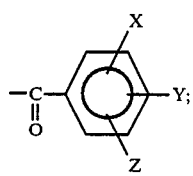

or a pharmaceutically acceptable salt thereof.

This invention also relates to methods for preparing the compounds of the present invention, to the use of such compounds in pharmaceutical compositions which are effective in increasing cardiac contractility in humans and to the uses of such compositions in the treatment of cardiac failure in humans and other mammals.

DETAILED DESCRIPTION

Certain of the compounds encompassed within the present invention, and particularly, compounds of Formula I, may exist in enolic or tautomeric forms, and all of these forms are considered to be included within the scope of this invention.

The compounds of this invention which have particular usefulness as cardiotonic agents are described by Formula I wherein the bicyclic thiazole substituent is:

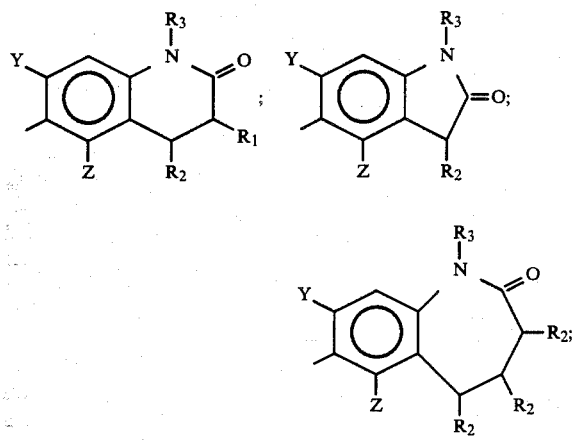

wherein:

$R_1$, $R_2$, $R_3$, Y and Z are as described above.

More preferred compounds are those disclosed by Formula I, wherein:

$R_4$ and $R_5$ form a carbon-carbon double bond.

Most preferred are those compounds within Formula I, wherein:

$R_7$ is hydrogen or methyl.

A special embodiment of the present invention comprises compounds of Formula I where $R_4$, $R_5$ and $R_6$ form a bicyclic fused ring system such as the following substituent groups:

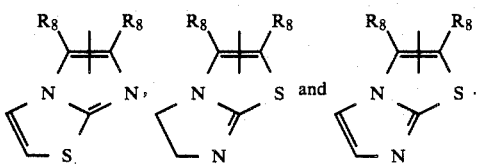

A special embodiment of the preferred compounds includes compounds of Formula II:

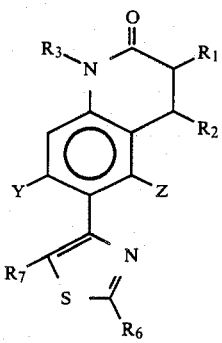

wherein:

$R_1$ and $R_2$ are H or lower alkyl;

$R_3$, $R_7$, Y and Z are as defined above;

$R_6$ is amino, lower alkylamino or dilower alkylamino; or a pharmaceutically acceptable salt thereof.

Other embodiments include those compounds according to Formula II wherein:

$R_1$ and $R_2$ form a double bond.

As employed above and throughout the disclosure, the following terms, unless otherwise indicated, shall be understood to have the following meanings:

"Bicyclic N-heteroaryl" means a fused aromatic bicyclic ring including a nitrogen atom in one of the two fused rings and where the total number of carbon atoms in the ring is no greater than about ten. Preferred rings include no more than nine carbon atoms. Exemplary groups include carbostyril, 3,4-dihydrocarbostyril, indolone, quinolinyl, di- and -tetrahydro quinolinyl, 1-benzazepinyl, 2,3,4,5-tetrahydro-1-benzazepinyl, among others.

"Alkyl" means a saturated aliphatic hydrocarbon which may be either straight- or branched-chained containing from about one to about 6 carbon atoms.

"Lower alkyl" means an alkyl group as above, having 1 to about 4 carbon atoms.

"Amidino" means a group of the formula

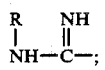

where R is H or lower alkyl.

"Guanidino" means a group of the formula

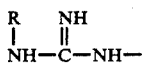

wherein R is H or lower alkyl.

"Hydroxy alkyl" means an alkyl group substituted by a hydroxy group. Hydroxy loweralkyl groups are preferred and include hydroxymethyl, 2-hydroxyethyl, 2-hydroxypropyl, and 3-hydroxypropyl.

"Alkoxy" means an alkyl oxy radical group. Lower alkoxy groups are preferred and include methoxy, ethoxy, n-propoxy, i-propoxy, see—propoxy, n-butoxy among others.

"Alkyl mercapto" means a radical of the formula —S—R where R is alkyl. Lower alkyl mercapto groups are preferred.

"Alkylsulfinyl" means a R—SO— radical where R is alkyl.

"Alkylsulfonyl" means a R—SO$_2$— radical where R is alkyl. Lower alkyl sulfonyl groups are preferred.

"Amino" means —NH$_2$ and "alkyl amino" means —NHR where R is alkyl. Lower alkyl amino groups are preferred.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds within the scope of Formula I may be prepared in accordance with the following reaction sequences.

The bicyclic portion of the compound can be prepared from an aniline as starting material, which is commercially available or is readily prepared according to methods known in the literature. N-acylation of the aniline with an α, β or γ-halo alkyl acylating agent, also either commercially available or prepared according to methods known in the art, results in an N-acyl intermediate which may be cyclized under Friedel-Crafts conditions with a Lewis acid such as aluminum chloride. Cyclization results in the bicyclic lactam of Formula III, below. To obtain compounds wherein R$_3$ is other than hydrogen, N-alkylation of the lactam nitrogen may be affected on the compound of Formula III or later on in the preparative sequence. Scheme I below illustrates the aforesaid reaction sequence.

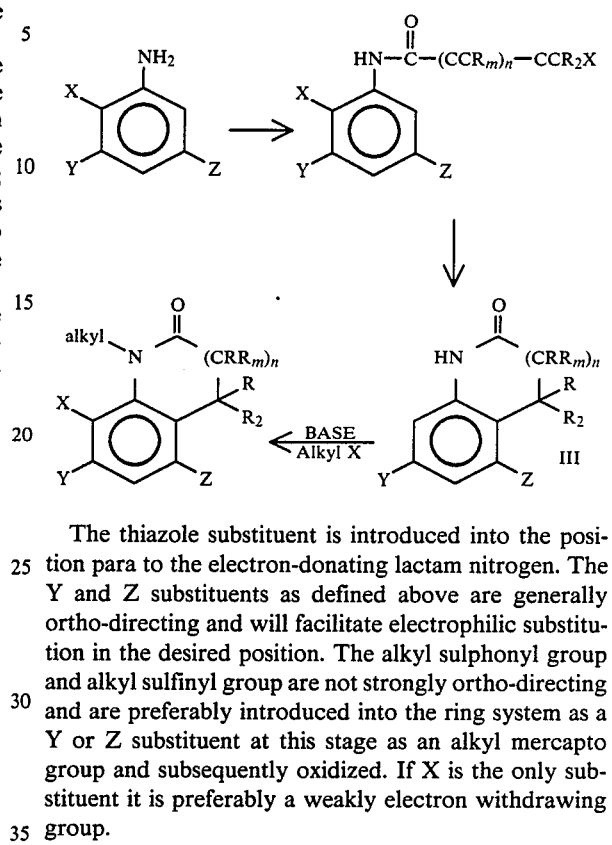

SCHEME I

The thiazole substituent is introduced into the position para to the electron-donating lactam nitrogen. The Y and Z substituents as defined above are generally ortho-directing and will facilitate electrophilic substitution in the desired position. The alkyl sulphonyl group and alkyl sulfinyl group are not strongly ortho-directing and are preferably introduced into the ring system as a Y or Z substituent at this stage as an alkyl mercapto group and subsequently oxidized. If X is the only substituent it is preferably a weakly electron withdrawing group.

Formation of the preferred 4-thiazole substituent may be effected by treating the compound of Formula III with an α-halo-acylchloride to effect the desired electrophilic aromatic substitution. The appropriately substituted 4-thiazole ring substituent is formed by treating the resulting keto compound with a thioamide compound such as thiourea, thioacetamide or thioamidinourea. The R$_4$ group may be introduced into the thiazole ring by utilizing an approprate derivative of thiourea, or by treatment of the unsubstituted thiazole intermediate compound with an appropriate electrophilic reagent. Scheme II below illustrates this reaction sequence.

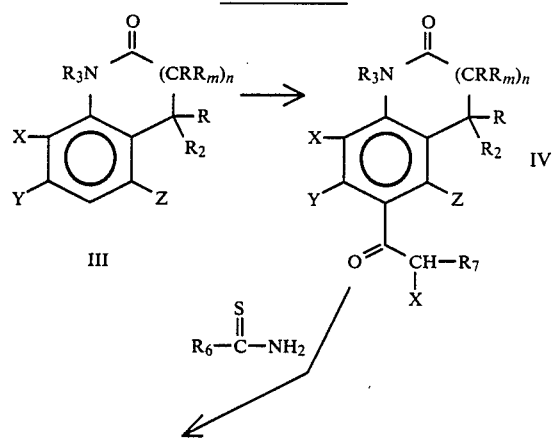

SCHEME II

-continued
SCHEME II

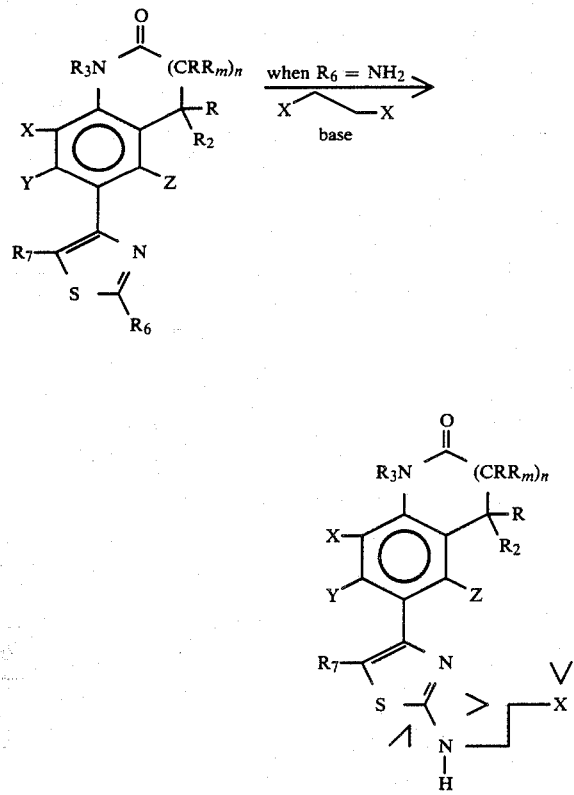

Formation of the dihydro-imidazo[2.1-b]thiazolyl compounds may be effected by treatment of the intermediate thiazole compound where $R_4$ is amino with a 1,2-dihaloethane reagent in the presence of base as depicted in Scheme II above.

A method for preparing the fully unsaturated imidazo[2.1-b]thiazolyl compounds comprises treating the intermediate of Formula IV with a 2-thio imidazole compound which are readily available or prepared by methods known in the art. The 2-thio group displaces the α-halo substituent and the imidazole nitrogen cyclizes to form the bicyclic structure.

Compounds where the bicyclic lactan is attached to the imidazolyl ring may be prepared by reacting the -halo intermediate IV with 2-amino thiazole. Scheme III below describes the aforesaid methods.

SCHEME III

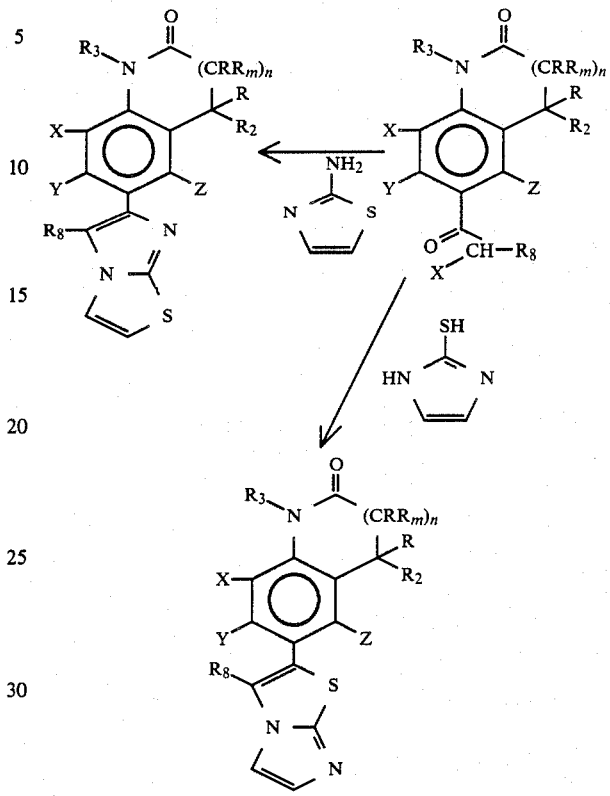

Exemplary starting materials which can be used to prepare compounds within the scope of the present invention are either commercially available or can be prepared by methods known in the art, and include: aniline; 2-methylaniline; 2-ethylaniline; 2-propylaniline; 2-butylaniline; 2-isopropylaniline; 2-(t-butyl)aniline; 3-methylaniline; 3-ethylaniline; 3-(n-propyl)aniline; 3-butylaniline; 3-isopropylaniline; 3-(t-butyl)aniline; 3,5-dimethylaniline; 3,5-diethylaniline; 3-methyl,5-ethylaniline; 2,3-dimethylaniline; 2,3,5-trimethylaniline; and 2,3-diethylaniline The N-acylating reagent for use in the reaction sequence in Scheme I above is preferably a lower alkyl acyl chloride, wherein the lower alkyl group is mono- or di-halo substituted, and is either commercially available or prepared by methods known in the literature. Exemplary acylating agents include: β-chloropropionyl chloride; β-bromopropionyl chloride; γ-chlorobutanoyl chloride; α-chloroacetyl chloride; α-chloroacetyl bromide; and the like.

The Friedal-Crafts cyclization may be effected by any known Friedal-Crafts cyclization reagent, such as aluminum chloride.

The electrophilic substitution reaction depicted in Scheme II above can utilize an α-halo lower alkyl acylating agent including: α-chloroacetyl chloride; α-bromoacetyl chloride; α-chloropropionylchloride; α-bromopropionyl chloride; α-chlorobutanoyl chloride; and the like.

As mentioned above, the formation of the thiazole substitutent from the compound of Formula IV utilizes a thioamide reagent of the formula

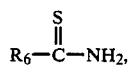

wherein $R_6$ is as described above, and is either commercially available or prepared according to methods disclosed in the literature.

The following are examples of preparations of compounds of the present invention.

EXAMPLE 1

The Preparation of 6-(2-Aminothiazol-4-yl)-3,4-Dihydrocarbostyril

Step 1. 3-Chloro-N-phenylpropionamide

A mixture of 3-chloropropionyl chloride (300 ml) and acetone (600 ml) is added dropwise to a refluxing mixture of aniline (575 ml) and acetone (600 ml). The reaction mixture is refluxed for one hour, cooled in an ice bath, and poured into a mixture of 6N HCl (500 ml) and water (3.5 l). The resulting solid is filtered, washed with water, and dried, yielding the desired product, M.P. 114°–115.5° C.

Step 2. 3,4-Dihydrocarbostyril

A solid mixture of 3-chloro-N-phenylpropionamide (50 g) and aluminum chloride (99.8 g) is heated resulting in the evolution of HCl gas. After gas evolution ceases, the mixture is kept warm for 30 minutes, allowed to cool to RT, and poured into ice, resulting in the formation of a grayish-white solid which is filtered, washed with water, and dried affording the desired product, M.P. 161°–163° C.

Step 3. 6-(Chloroacetyl)-3,4-dihydrocarbostyril

Chloroacetyl chloride (64 g) is added to a stirred solution of 3,4-dihydrocarbostyril (40 g) and aluminum chloride (76 g) in methylene chloride (500 ml). The reaction mixture is refluxed for 3 hours, cooled to RT and poured into ice water affording a white solid which is filtered, washed with water, dried, and recrystallized from ethanol, yielding the desired product.

Step 4. 6-(2-Aminothiazol-4-yl)-3,4-dihydrocarbostyril 6-(Chloroacetyl)-3,4-dihydrocarbostyril (7 g), thiourea (2.6 g) and absolute ethanol (250 ml) is stirred under reflux for two hours, cooled in an ice bath, filtered, and the filtered solid washed with ether and dried. The solid is suspended in aqueous sodium bicarbonate and stirred for 30 minutes, filtered, washed with isopropanol, dried and refluxed in methanol (300 ml) overnight. The resulting solid is filtered, suspended in boiling methanol (300 ml) and methane sulfonic acid (2.8 ml) added, resulting in the formation of a precipitate which is filtered, twice recrystallized from ethanol/DMF affording the desired product as the methane sulfonic acid salt, M.P. >250° C.

EXAMPLE 2

The Preparation of 6-(2-Methylthiazol-4-yl)-3,4-Dihydrocarbostyril 6-(Chloroacetyl)-3,4-dihydrocarbostyril (7 g), thioacetamide (2.7 g) and absolute ethanol (250 ml) are stirred under reflux for two hours. The cooled reaction mixture is filtered and the filtered solid washed with ether, dried, and suspended in aqueous sodium bicarbonate for 30 minutes. The suspendant is filtered, washed with isopropanol, dried and dissolved in boiling methanol to which methane sulfonic acid (1.6 ml) is added. The methanol solution is cooled in an ice bath, and the precipitate filtered and recrystallized from ethanol, yielding the desired product as the methane sulfonic acid salt, M.P. >250° C.

EXAMPLE 3

The Preparation of 6-(2-Guanidinothiazol-4-yl)-3,4-Dihydrocarbostyril

A mixture of 6-(chloroacetyl)-3,4-dihydrocarbostyril (7 g), amidinothiourea (3.8 g) and absolute ethanol (250 ml) is stirred under reflux for about 24 hours. The reaction mixture is cooled to ice bath temperature and the precipitate filtered, washed with ethanol, and dried. The solid is suspended in aqueous sodium hydroxide, filtered, the filtered solid washed with water, and dried in vacuo. The dried solid is recrystallized from 50% aqueous DMF, and dried in vacuo yielding the desired product, M.P. >250° C.

EXAMPLE 4

The Preparation of 5-(2-Amino-4-Methylthiazol-4-yl)-3,4-Dihydrocarbostyril

Step 1. 6-(α-Bromopropionyl)-3,4-dihydrocarbostyril

A mixture of α-bromopropionyl chloride (50 g) in methylene chloride (350 ml) is added to a stirred mixture of 3,4-dihydrocarbostyril (21.8 g) and aluminum chloride (44.8 g). The reaction mixture is stirred under reflux for four hours, poured into an ice water mixture, stirred for 30 minutes and the solid filtered, washed with water, dried, and recrystallized from isopropanol affording the desired product.

Step 2. 5-(2-Amino-4-methylthiazol-4-yl)-3,4-dihydrocarbostyril

A suspension of 6-(α-bromopropionyl)-3,4-dihydrocarbostyril (7 g) and thiourea (1.9 g) in absolute ethanol (300 ml) is stirred at reflux for about 4 hours. The reaction mixture is cooled to RT, filtered and the solid washed with ethanol, ether, dried, and suspended in aqueous sodium bicarbonate (300 ml) for one hour. The solid is filtered, washed with water and isopropanol, dried and suspended in ethanol (200 ml) to which methane sulfonic acid (1.7 ml) is added. The ethanol suspension is heated to boiling, concentrated and allowed to cool. The resulting precipitate is filtered, washed with isopropanol, and dried, affording the desired product as the methane sulfonic acid salt, M.P. 249°–250° C.

EXAMPLE 5

The Preparation of 6-(2,5-Dimethylthiazol-4-yl)-3,4-Dihydrocarbostyril

A mixture of 6-(α-bromopropionyl)-3,4-dihydrocarbostyril (7 g), thioacetamide (2 g) and absolute ethanol (250 ml) is stirred under reflux for 3 hours and allowed to cool overnight. The resulting white precipitate is filtered, washed with ether, dried and suspended in aqueous sodium bicarbonate for 30 minutes. The neutralized solid is filtered, washed with water, isopropanol, and recrystallized from isopropanol affording the desired product, M.P. 241°–242° C.

EXAMPLE 6

The Preparation of 6-(2-Guanidino-5-Methylthiazol-4-yl)-3,4-Dihydrocarbostyril A mixture of 6-(α-bromopropionyl)-3,4-dihydrocarbostyril (7 g), amidinothiourea (3.1 g) and absolute ethanol (250 ml) is stirred under reflux overnight. The reaction mixture is cooled to ice bath temperature, and the solid filtered, washed with ethanol, dried, and suspended in aqueous sodium hydroxide. The neutralized solid is filtered, washed with water, dried and recrystallized from 50% aqueous DMF affording the desired product, M.P. >250° C.

EXAMPLE 7

The Preparation of 6-(2-Amino-5-Ethylthiazol-4-yl)-3,4-Dihydrocarbostyril

Step 1. 6-(α-Bromobutanoyl)-3,4-dihydrocarbostyril

A solution of α-bromobutanoyl chloride (78.9 g) in methylene chloride (50 ml) is added to a stirred mixture of 3,4-dihydrocarbostyril (31.3 g) and aluminum chloride (59.6 g) in methylene chloride (300 ml). The reaction mixture is stirred at reflux for about 3.5 hours, cooled, poured into a mixture of ice and water, resulting in the formation of a white precipitate which is filtered, washed with water, dried, and recrystallized from isopropanol, affording the desired product.

Step 2. 6-(2-Amino-5-ethylthiazol-4-yl)-3,4-dihydrocarbostyril

A mixture of 6-(α-bromobutanoyl)-3,4-dihydrocarbostyril (7 g), thiourea (1.9 g) and absolute ethanol (250 ml) is stirred at reflux for 4 hours. The reaction mixture is cooled in an ice bath and the solid filtered, washed with ether, dried and suspended in aqueous sodium bicarbonate for 30 minutes. The neutralized solid is filtered, washed with water and isopropanol, and dried. The dried solid is suspended in boiling THF to which methane sulfonic acid is added. The resulting THF solution is concentrated and cooled in an ice bath resulting in the formation of a precipitate which is filtered, washed with ether, dried in vacuo and twice recrystallized from acetonitrile and isopropanol affording the desired product as the methane sulfonic salt, M.P. 221°-223° C.

EXAMPLE 8

The Preparation of 6-(6-Ethyl-2-Methylthiazol-4-yl)-3,4-Dihydrocarbostyril

A mixture of 6-(α-bromobutanoyl)-3,4-dihydrocarbostyril (7 g), thioacetamide (2 g) and absolute ethanol (250 ml) is stirred under reflux for about 72 hours. The reaction mixture is evaporated and the residue treated with aqueous sodium carbonate. The aqueous mixture is partitioned between water and ethyl acetate and the organic phase dried over sodium sulfate, filtered and evaporated affording a solid residue which is three times recrystallized from toluene and cyclohexane affording the desired product. M.P. 186°-187° C.

EXAMPLE 9

The Preparation of 6-(2-Guanidino-5-Ethylthiazol-4-yl)-3,4-Dihydrocarbostyril A mixture of 6-(α-bromobutanoyl)-3,4-dihydrocarbostyril (7 g), amidinothiourea (2.9 g) and absolute ethanol (250 ml) is stirred at reflux overnight. The reaction mixture is cooled to ice bath temperature and the solid filtered, washed, dried and suspended in aqueous sodium hydroxide. The neutralized solid is filtered, washed with water, dried in vacuo and recrystallized from 50% aqueous DMF and boiling water affording the desired product, M.P. 230° C. (dec).

EXAMPLE 10

The Preparation of 6-(2-Amino-5-Methylthiazol-4-yl)-N-Methyl-3,4-Dihydrocarbostyril Step 1. N-Methyldihydrocarbostyril A solution of 3,4-dihydrocarbostyril (20 g) in DMSO (100 ml) is added to a suspension of KOH (31.4 g) in DMSO (50 ml). Methyl iodide (39.7 g) in DMSO (25 ml) is added to the reaction mixture and the mixture is stirred under an atmosphere of $N_2$ at RT. After 2 hours a second portion of methyl iodide (20 g) is added and after 3 hours a third portion of methyl iodide (20 g) is added and stirring continued for 4.5 hours. The reaction mixture is diluted with chloroform (200 ml), quenched with sat'd aq. $NH_4Cl$, separated, extracted with chloroform, washed with $H_2O$ and dried. The organic extracts are filtered and concentrated in vacuo affording the desired product as an oil.

Step 2. 6-(2-Bromopropionyl)-N-methyl-3,4-dihydrocarbostyril

2-Bromopropionyl chloride (41.1 g) is added dropwise to a suspension of the N-methyl product obtained in Step 1. above (18.6 g) and $AlCl_3$ (37.4 g) in chloroform (350 ml). The stirred reaction mixture is refluxed for 4 hours, cooled to RT and stirred with an ice/water mixture for 45 minutes. The reaction mixture is separated, extracted with methylene chloride and the combined extracts are washed with $H_2O$, 5% aq. bicarbonate, $H_2O$, dried, filtered and concentrated in vacuo, yielding a viscous oil, which is crystallized from ethyl acetate affording the desired product, M.P. = 86°-88° C.

Step 3. 6-(2-Amino-5-methylthiazol-4-yl)-N-methyl-3,4-dihydrocarbostyril

A solution of the 2-bromo compound obtained in Step 2. above (3 g) and thiourea (0.77 g) in absolute EtOH (350 ml) is stirred under reflux overnight. A second portion of thiourea (0.15 g) is added to the reaction mixture and reflux is continued for 2 hours. The mixture is cooled to RT in an ice bath and filtered. The filtered solid is washdd with absolute EtOH and dried affording the desired product as the hydrobromide salt, which is recrystallized from DMF, M.P. = 246°-248° C. (dec).

EXAMPLE 11

The Preparation of 6-(2-Aminothiazol-4-yl)-N-Methyl-3,4-Dihydrocarbostyril

Step 1. 6-(Bromoacetyl)-N-methyl-3,4-dihydrocarbostyril

Bromoacetyl chloride (28.3 g) is added dropwise to a suspension of N-methyl-tetrahydroquinolin-2-one (14.7 g) and AlCl$_3$ (26.7 g) in methylene chloride (400 ml), and the reaction mixture is refluxed for 5 hours. The reaction mixture is cooled to RT, stirred with an ice/-water mixture for 30 minutes, diluted with methylene chloride (200 ml) and separated. The aqueous layer is extracted with methylene chloride, and the combined organic extracts are washed with H$_2$O, dried, filtered and concentrated in vacuo, yielding a crude solid which is recrystallized from isopropanol affording the desired product as a solid.

Step 2. 6-(2-Aminothiazol-4-yl)-N-methyl-3,4-dihydrocarbostyril

A mixture of the bromoacetyl compound obtained in Step 1. above (6 g) and thiourea (1.62 g) in absolute ethanol (400 ml) is stirred under reflux for 4 hours. A second portion of thiourea (0.2 g) is added to the mixture which is refluxed for 3 hours. The mixture is filtered while hot yielding the desired product as a solid which is recrystallized from methanol, M.P.=233°–235° C. (dec).

EXAMPLE 12

The Preparation of 5-(2-Amino-5-Methylthiazol-4-yl)Oxindole

Step 1. 5-(2-Bromopropionyl)oxindole

A solution of bromopropionyl chloride (2.58 g) in methylene chloride (10 ml) is added to a stirred suspension of oxindole (1 g) and AlCl$_3$ (2.27 g) in methylene chloride (35 ml). The suspension is refluxed for 4 hours, cooled to RT, poured into an ice/water mixture, stirred for 30 minutes and then filtered affording the desired product.

Step 2. 5-(2-Amino-5-methylthiazol-4-yl)oxindole.hydrochloride

A solution of the 2-bromo compound obtained in Step 1. above (6 g) and thiourea (1.9 g) in absolute EtOH (350 ml) is refluxed overnight, cooled, and filtered yielding a solid which is triturated in warm absolute EtOH, filtered and dried under vacuum affording the hydrobromide salt, M.P. >250° C.

Step 3. 5-(2-Amino-5-methylthiazol-4-yl)oxindole.methanesulfonate

A suspension of the hydrobromide of Step 2. above (2 g) in sat'd aq. bicarbonate is stirred for one hour. The solid is filtered, air dried and suspended in absolute ethanol. Methanesulfonic acid (0.1 ml) is added to the mixture which is heated to boiling, cooled and filtered affording the desired product, M.P. >250° C.

EXAMPLE 13

The Preparation of 5-(2-Aminothiazol-4-yl)Oxindole

Step 1. 5-(α-Bromoacetyl)oxindole

A solution of bromoacetyl chloride (14.17 g) in methylene chloride (30 ml) is added dropwise to a stirred suspension of oxindole (6 g) and AlCl$_3$ (13.31 g) in methylene chloride (200 ml). The reaction mixture is refluxed for 4 hours, cooled to RT, poured with stirring into an ice/water mixture, stirred for 30 minutes, filtered and washed with methylene chloride yielding the desired product as a solid which is recrystallized from isopropanol.

Step 2. 5-(2-Aminothiazol-4-yl)oxindole

A solution of 5-(α-bromoacetyl)oxindole (5 g) and thiourea (1.67 g) in absolute EtOH (250 ml) is refluxed for 30 minutes. The reaction mixture is cooled to RT, filtered, and washed with absolute EtOH affording the desired product. The free base is converted to its methanesulfonate salt by the procedure previously described in Example 12, affording the desired product, M.P.=244°–246° C.

The compounds listed in Tables I, II, III, IV, V and VI below may be prepared according to the exemplary preparations described above using analogous reaction conditions and starting materials, which are either commercially available or prepared by methods known to those skilled in the art.

TABLE I

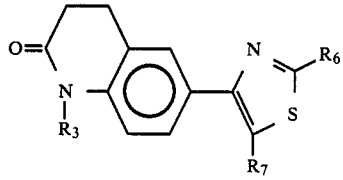

| R$_3$ | R$_7$ | R$_6$ |
|---|---|---|
| H | H | —NH$_2$ |
| H | CH$_3$ | —NH$_2$ |
| H | H | —NHCH$_3$ |
| H | C$_2$H$_5$ | —NHC$_2$H$_5$ |
| H | H | —N(CH$_3$)$_2$ |
| H | C$_3$H$_7$ | —N(CH$_3$)$_2$ |
| H | H | —N(H)—C(=NH)—NH$_2$ |
| H | CH$_3$ | —N(H)—C(=NH)—NH$_2$ |
| H | H | —C(=NH)—NH$_2$ |
| H | C$_2$H$_5$ | —C(=NH)—NH$_2$ |
| H | H | —C(=NH)—NHCH$_3$ |
| H | CH$_3$ | NH—C(=NH)—NHCH$_3$ |
| CH$_3$ | H | NH$_2$ |
| C$_2$H$_5$ | CH$_3$ | NH$_2$ |
| CH$_3$ | H | NHCH$_3$ |
| C$_2$H$_5$ | C$_2$H$_5$ | NHC$_2$H$_5$ |
| CH$_3$ | H | N(CH$_3$)$_2$ |
| C$_2$H$_5$ | C$_3$H$_7$ | N(CH$_3$)$_2$ |
| CH$_3$ | H | —N(H)—C(=NH)—NH$_2$ |
| C$_2$H$_5$ | CH$_3$ | —N(H)—C(=NH)—NH$_2$ |
| CH$_3$ | H | —C(=NH)—NH$_2$ |
| C$_2$H$_5$ | C$_2$H$_5$ | —C(=NH)—NH$_2$ |
| CH$_3$ | H | —C(=NH)—NHCH$_3$ |

TABLE I-continued

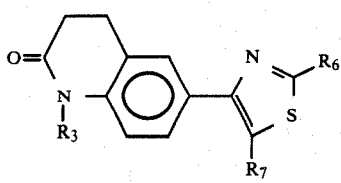

| R₃ | R₇ | R₆ |
|---|---|---|
| C₂H₅ | CH₃ | NH−C(=NH)−NHCH₃ |
| C₃H₇ | H | NH₂ |

TABLE II

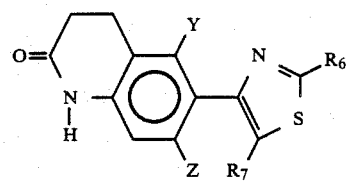

| Y, Z | R₇ | R₆ |
|---|---|---|
| H, OCH₃ | CH₃ | NH₂ |
| H, OCH₃ | H | NHCH₃ |
| H, OCH₃ | C₂H₅ | NHC₂H₅ |
| CH₃, H | H | N(CH₃)₂ |
| CH₃, H | C₃H₇ | N(CH₃)₂ |
| CH₃, H | H | N(H)−C(=NH)−NH₂ |
| CH₃, CH₃ | CH₃ | N(H)−C(=NH)−NH₂ |
| CH₃, CH₃ | H | −C(=NH)−NH₂ |
| CH₃, OCH₃ | C₂H₅ | −C(=NH)−NH₂ |
| OCH₃, OCH₃ | H | −C(=NH)−NHCH₃ |
| OCH₃, OCH₃ | CH₃ | NH−C(=NH)−NHCH₃ |
| OH, H | H | NH₂ |
| OH, OH | CH₃ | NH₂ |
| SO₂CH₃, H | H | NHCH₃ |
| H, SO₂CH₃ | C₂H₅ | NHC₂H₅ |
| H, CH₃ | H | N(CH₃)₂ |
| H, CH₃ | C₃H₇ | N(CH₃)₂ |
| H, CH₃ | H | N(H)−C(=NH)−NH₂ |
| H, OCH₃ | CH₃ | N(H)−C(=NH)−NH₂ |
| OCH₃, OCH₃H | H | −C(=NH)−NH₂ |

TABLE II-continued

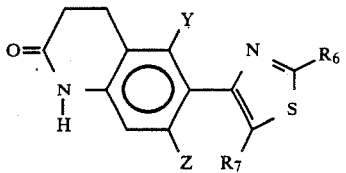

| Y, Z | R₇ | R₆ |
|---|---|---|
| OCH₃, OCH₃ | C₂H₅ | −C(=NH)−NH₂ |
| H, H | H | −C(=NH)−NHCH₃ |
| H, H | CH₃ | NH−C(=NH)−NHCH₃ |
| SO₂CH₃, H | H | NH₂ |
| SO₂CH₃, H | CH₃ | NH₂ |

TABLE III

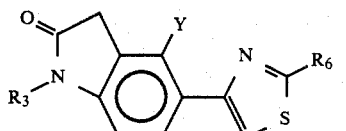

| R₃ | Y,Z | R₈ | R₆ |
|---|---|---|---|
| H | H,H | H | NHCH₃ |
| H | H,H | C₂H₅ | NHC₂H₅ |
| H | H,H | H | N(CH₃)₂ |
| H | H,H | C₃H₇ | N(CH₃)₂ |
| H | H,H | H | N(H)−C(=NH)−NH₂ |
| H | H,H | CH₃ | N(H)−C(=NH)−NH₂ |
| H | H,H | H | −C(=NH)−NH₂ |
| H | H,H | C₂H₅ | −C(=NH)−NH₂ |
| H | H,H | H | −C(=NH)−NHCH₃ |
| H | H,H | CH₃ | NH−C(=NH)−NHCH₃ |
| H | H,H | H | NH₂ |
| H | H,H | CH₃ | NH₂ |
| H | H,H | H | N(CH₃)₂ |
| CH₃ | H,OCH₃ | H | NHCH₃ |
| CH₃ | H,OCH₃ | C₂H₅ | NHC₂H₅ |
| CH₃ | H,OCH₃ | H | N(CH₃)₂ |
| CH₃ | CH₃,H | C₃H₇ | N(CH₃)₂ |
| CH₃ | CH₃,H | H | N(H)−C(=NH)−NH₂ |

TABLE III-continued

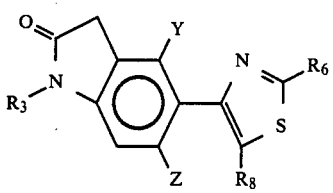

| R₃ | R₈ | R₆ | |
|---|---|---|---|
| CH₃ | CH₃,H | CH₃ | H NH<br>\| \|\|<br>N—C—NH₂ |
| | X,Y | | |
| CH₃ | CH₃,CH₃ | H | NH<br>\|\|<br>—C—NH₂ |
| CH₃ | CH₃,CH₃ | C₂H₅ | NH<br>\|\|<br>—C—NH₂ |
| CH₃ | CH₃,CH₃ | H | NH<br>\|\|<br>—C—NHCH₃ |
| CH₃ | CH₃,OCH₃ | CH₃ | NH<br>\|\|<br>NH—C—NHCH₃ |
| CH₃ | OCH₃,CH₃ | H | NH₂ |
| CH₃ | OCH₃,OCH₃ | H | NH₂ |
| CH₃ | OCH₃,OCH₃ | H | NH₂ |
| CH₃ | OH,H | H | NH₂ |
| CH₃ | OH,OH | H | NH₂ |

TABLE IV

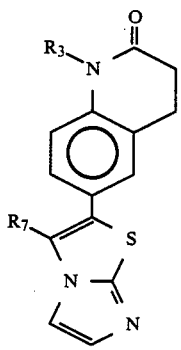

| R₃ | R₇ |
|---|---|
| H | H |
| CH₃ | H |
| C₂H₅ | H |
| C₃H₇ | H |
| H | CH₃ |
| CH₃ | CH₃ |
| C₂H₅ | CH₃ |
| C₃H₇ | CH₃ |

TABLE V

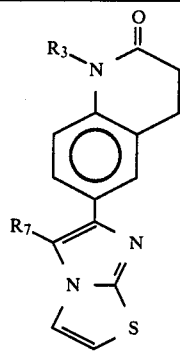

| R₃ | R₇ |
|---|---|
| H | H |
| CH₃ | H |
| C₂H₅ | H |
| C₃H₇ | H |
| H | CH₃ |
| CH₃ | CH₃ |
| C₂H₅ | CH₃ |
| C₃H₇ | CH₃ |

TABLE VI

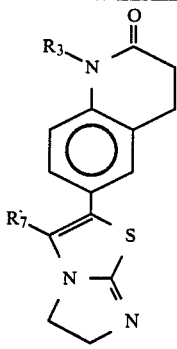

| R₃ | R₇ |
|---|---|
| H | CH₃ |
| CH₃ | H |
| C₂H₅ | CH₃ |
| C₃H₇ | H |
| H | CH₃ |
| CH₃ | H |
| C₂H₅ | CH₃ |
| C₃H₇ | CH₃ |

The compounds of Formula I possess positive inotropic activity and are useful as cardiotonic agents in the treatment of humans and other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

ANESTHETIZED DOG PROCEDURE

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastatic pressure and dP/dt. Lead II ECG and heart rate are also monitored. All parameters are measured on a Beckman Dynagraph.

The results of the anesthetized dog test show that the compounds of this invention exhibit positive inotropic activity and show dose related increases in contractile force with relatively small increases in heart rate.

A second test procedure which has been found to be an efficient means for ascertaining the inotropic activity of the compounds of this invention is described below.

GUINEA PIG ATRIA INOTROPIC SCREENING AT LOW CALCIUM CONCENTRATIONS

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$, 25.00; glucose, 11.66; and $CaCl_2$, 1.25) gassed with a mixture of 95% $O_2$-5% $CO_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is acheived via a pair of platinum or silver electrodes placed on opposite sides of the tissue. Electrodes are made from 20-gauge silver wire wound into a tight coil approximately 12-14 mm in diameter. Electrodes are connected to a Grass stimulator via a Grass constant current unit. Tissues are driven at 90 pulses per minute with a 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions are calculated via the method of Finney (1971) and compared using Student's t-test.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

We claim:

1. A compound according to the formula

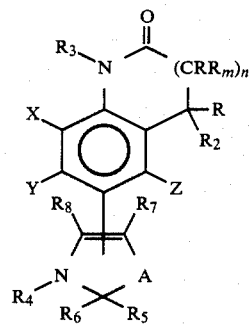

wherein:
m is 1;
n is 1;

$R_m$ is $R_1$;
A is S;
X, Y and Z are each independently hydrogen, alkyl, alkoxy, alkylmercapto, alkylsulfinyl or alkylsulfonyl;
R and $R_3$ are each independently hydrogen or lower alkyl;
$R_1$ and $R_2$ are each independently hydrogen, lower alkyl or both $R_1$ and $R_2$ form a carbon-carbon double bond;
$R_4$ and $R_5$ together form a carbon-nitrogen double bond;
$R_6$ is hydrogen, alkyl, amino, mono- or di-alkylamino, 3,4-dimethoxy benzylamino, guanidino, amidino, hydroxyl, hydroxyalkyl, hydroxyalkylamino, aminoalkylamino, di-alkylaminoalkylamino, aminoalkyl, mono- or di-alkylaminoalkyl,

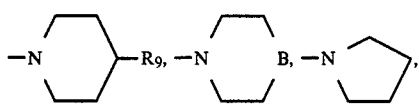

one of $R_7$ or $R_8$ is hydrogen or lower alkyl, and one of $R_7$ or $R_8$ represents the carbon-carbon single bond to the position on the fused bicycle ring ortho to the Y and Z groups;
$R_9$ is H or alkyl;
B is $NR_{10}$, oxygen or sulfur; and
$R_{10}$ is H, alkyl, or

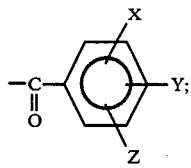

or a pharmaceutically acceptable salt thereof.

2. A compound according to claim 1, wherein:
$R_7$ is hydrogen or lower alkyl; and
$R_1$ and $R_2$ together form a double bond.

3. A compound according to claim 1, wherein $R_7$ is hydrogen or lower alkyl.

4. A method of treating congestive heart failure comprising administering to a patient in need of such treatment an effective cardiotonic amount of a compound of claim 1.

5. A method of increasing cardiac contractility in humans and other mammals comprising administering thereto an effective inotropic amount of a compound of claim 1.

6. A cardiotonic composition comprising an effective cardiotonic amount of a compound of claim 1 and a pharmaceutically acceptable carrier.

7. A compound of the formula:

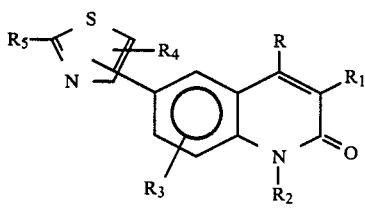

wherein
R, $R_1$, $R_2$ and $R_4$ are independently hydrogen or $C_1$-$C_4$ alkyl;
$R_3$, which is attached at the 5-, 7-, or 8-position of the quinoline nucleus, is hydrogen, $C_1$-$C_4$ alkyl, $C_1$-$C_4$ alkoxy, $C_1$-$C_4$ alkylthio, $C_1$-$C_4$-alkylsulfinyl or $C_1$-$C_4$ alkysulfonyl;
$R_5$ is hydrogen, $C_1$-$C_4$ alkyl, hydroxy($C_1$-$C_4$)alkyl, amino, $C_1$-$C_4$ alkylamino or di($C_1$-$C_4$)alkylamino;
the dotted line between the 3- and 4-positions represents an optional double bond; and pharmaceutically-acceptable salts thereof.

8. A compound according to the formula:

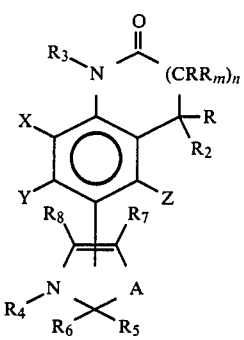

wherein:
m is 1;
n is 1;
$R_m$ is $R_1$;
A is N or S, provided that A is N only when A and $R_6$ together form a double bond in an imidazo[2.1-b]thiazole ring system;
X, Y and Z are each independently hydrogen, alkyl, alkoxy, hydroxy, alkylmercapto, alkylsulfinyl or alkylsulfonyl;
R and $R_3$ are each independently hydrogen or lower alkyl;
$R_1$ and $R_2$ are each independently hydrogen, lower alkyl or both $R_1$ and $R_2$ form a carbon-carbon double bond;
$R_4$ and $R_5$ together with the atoms to which they are attached form an imidazo[2.1-b]thiazole ring system including two additional carbon atoms and either one sulfur atom or one additional nitrogen atom;
$R_6$ together with either $R_5$ or A form a carbon-nitrogen double bond in said imidazo[2.1-b]thiazole ring system;
one of $R_7$ or $R_8$ is hydrogen or lower alkyl, and one of $R_7$ or $R_8$ represents the carbon-carbon single bond to the position on the fused bicycle ring ortho to the Y and Z groups;
or a pharmaceutically acceptable salt thereof.

9. A compound according to the formula

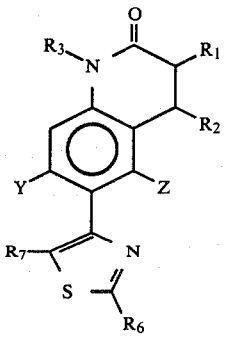

wherein:

$R_1$, $R_2$, $R_3$ and $R_7$ are each independently hydrogen or lower alkyl;

Y and Z are each independently hydrogen, lower alkyl, lower alkoxy, hydroxy, lower alkylmercapto, lower alkylsulfinyl or lower alkylsulfonyl;

$R_6$ is hydrogen, lower alkyl, amino, mono- or di-loweralkylamino, 3,4-dimethoxy benzylamino, guanidino, amidino, hydroxyl, hydroxyloweralkyl, hydroxyloweralkylamino, aminoloweralkylamino, mono- or di-loweralkylaminoloweralkylamino, aminoloweralkyl, mono- or di-loweralkylaminoloweralkyl, aminoloweralkyl,

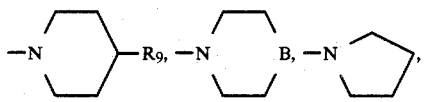

$R_9$ is H or alkyl;

B is $NR_{10}$, oxygen or sulfur; and $R_{10}$ is H, alkyl, or

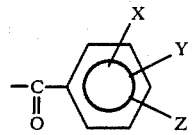

or a pharmaceutically acceptable salt thereof.

10. A compound according to claim 9, wherein $R_7$ is H; and
$R_6$ is amino, lower alkylamino or dilower alkylamino.

11. A compound according to claim 10, wherein $R_3$ is hydrogen.

12. A compound according to claim 9 which is 6-(2-aminothiazol-4-yl)-3,4-dihydrocarbostyril, or a pharmaceutically acceptable salt thereof.

13. A compound according to claim 9 which is 6-(2-methylthiazol-4-yl)-3,4-dihydrocarbostyril, or a pharmaceutically acceptable salt thereof.

14. A compound according to claim 9 which is 6-(2-guanidinothiazol-4-yl)-3,4-dihydrocarbostyril, or a pharmaceutically acceptable salt thereof.

15. A compound according to claim 9 which is 6-(2-amino-5-methylthiazol-4-yl)-3,4-dihydrocarbostyril, or a pharmaceutically acceptable salt thereof.

16. A compound according to claim 9 which is 6-(2,5-dimethylthiazol-4-yl)-3,4-dihydrocarbostyril, or a pharmaceutically acceptable salt thereof.

17. A compound according to claim 9 which is 6-(2-guanidino-5-methylthiazol-4-yl)-3,4-dihydrocarbostyril, or a pharmaceutically acceptable salt thereof.

18. A compound according to claim 9 which is 6-(2-amino-5-ethylthiazol-4-yl)-3,4-dihydrocarbostyril, or a pharmaceutically acceptable salt thereof.

19. A compound according to claim 9 which is 6-(5-ethyl-2-methylthiazol-4-yl)-3,4-dihydrocarbostyril, or a pharmaceutically acceptable salt thereof.

20. A compound according to claim 9 which is 6-(2-guanidino-5-ethylthiazol-4-yl)-3,4-dihydrocarbostyril, or a pharmaceutically acceptable salt thereof.

21. A compound according to claim 9 which is 6-(2-amino-5-methylthiazol-4-yl)-N-methyl-3,4-dihydrocarbostyril, or a pharmaceutically acceptable salt thereof.

22. A compound according to claim 9 which is 6-(2-aminothiazol-4-yl)-N-methyl-3,4-dihydrocarbostyril, or a pharmaceutically acceptable salt thereof.

* * * * *